United States Patent [19]

Lang et al.

[11] Patent Number: 5,506,112
[45] Date of Patent: Apr. 9, 1996

[54] REAGENT USED FOR DETERMINING FACTOR VIII ACTIVITY

[75] Inventors: Hartmut Lang; Berta Moritz; Manfred Oberreither; Olga Lukas, all of Vienna, Austria

[73] Assignee: Immuno Aktiengesellschaft, Austria

[21] Appl. No.: 819,456

[22] Filed: Jan. 10, 1992

[30] Foreign Application Priority Data

Jan. 25, 1991 [AT] Austria ........................ 164/91

[51] Int. Cl.$^6$ ................ C12Q 1/56; C12P 21/04; G01N 33/53; A61K 35/14
[52] U.S. Cl. ................ 435/13; 435/69.6; 435/975; 436/69; 530/383; 530/384; 424/529
[58] Field of Search ............ 435/13, 69.6, 948; 514/2, 21; 436/69; 530/383, 407, 806, 384, 381

[56] References Cited

U.S. PATENT DOCUMENTS

| | | | |
|---|---|---|---|
| 4,348,315 | 9/1982 | Birger et al. | 530/806 |
| 4,395,396 | 7/1983 | Eibl et al. | 530/384 |
| 4,657,894 | 4/1987 | Zimmerman et al. | 530/381 |
| 4,672,030 | 6/1987 | Witt | 435/13 |
| 4,786,726 | 11/1988 | Smith | 530/384 |
| 4,965,199 | 10/1990 | Capon et al. | 435/948 |
| 5,059,525 | 10/1991 | Bartl et al. | 435/13 |
| 5,061,789 | 10/1991 | Moller et al. | 530/384 |
| 5,091,363 | 2/1992 | Heimburger et al. | 514/21 |

FOREIGN PATENT DOCUMENTS

| | | |
|---|---|---|
| 0050061 | 9/1981 | European Pat. Off. . |
| 0131740 | 6/1984 | European Pat. Off. . |
| 159311 | 2/1985 | European Pat. Off. . |

OTHER PUBLICATIONS

Wagenvoord et al., "Development of a Simple Chromogenic Factor VIII Assay for Clinical Use", Haemostasis, 19:196–204 (1989).

Dieijen et al., "The Role of Phospholipid and Factor VIII$_a$ in the Activation of Bovine Factor X", J. Bio. Chem. 256:3433–3422 (1981).

Monroe et al., Archives of Biochemistry and Biophysics, vol. 238, No. 2, Mayl, pp. 490–496, 1985.

Elodi et al., Mol Aspects Med, (1983) 6(4) 291–353.

Griffith et al., J. Clin. Invest., vol. 75, Jan. 1985, pp. 4–10.

Sugimoto et al., Abstract; J. Biochem, 104(6), pp. 878–880, Dec. 1988.

Dieijen et al., "Spectrophotometric method for the assay of human blood coagulation factor VIII", Haemostasis, 17:14–24 (1987).

Beals et al., "The kinetic assembly of the intrinsic bovine factor X activation system", Archives of Biochemistry and Biophysics, 268:485–501 (1989).

Griffith et al., "Measurement of human factor IXa activity in an isolated factor X activation system", Thrombosis Research, 27:289–301 (1982).

Van de Waart et al., "A simple screening test for protein S activity in human plasma", Haemostasis, 16:72 (1986).

Primary Examiner—Douglas W. Robinson
Assistant Examiner—Louise Leary
Attorney, Agent, or Firm—Brumbaugh, Graves, Donohue & Raymond

[57] ABSTRACT

To determine the factor VIII activity of a sample, the latter is reacted with a reagent containing thrombin, factor IXaβ, phospholipids and calcium ions so as to form a factor VIIIa-factor IXa-phospholipid-calicum ion-containing complex. This complex is reacted with factor X so as to obtain activated factor X. The obtained factor Xa is reacted with chromogenic substrate so as to form a substance to be determined spectrophotometrically. Complex formation and activation of factor X are effected in one stage: The sample is mixed with a mixture of human thrombin, phospholipids, calcium ions, human factor IXaβ, human factor X and, if desired, human factor XIa and human factor XIIa, as a complex-forming reagent.

18 Claims, No Drawings

REAGENT USED FOR DETERMINING FACTOR VIII ACTIVITY

The invention relates to a reagent for determining factor VIII activity as well as to a method of determining the factor VIII activity of a sample.

An assay for determining factor VIII activity was described by R. J. Wagenvoord et al. for clinical use (Haemostasis 19, 196–204 (1989)). According to that method, a mixture of factor IXa, thrombin, calcium ions and phospholipids is added to a factor VIII-containing sample as reagent 1, thus activating the factor VIII to be assayed. Subsequently, activated factor VIII forms a complex with factor IXa, the phospholipids and the calcium ions, which complex is capable of activating factor X, which must be added later on as additional reagent (reagent 2). A chromogenic substrate may be split by activated factor X in a known manner, the factor VIII activity of the assaying sample being calculable from the amount of substance formed and to be determined photometrically. The factor IXa contained in the complex forming reagent and the thrombin contained therein as well as the factor X used to form activated factor Xa are of bovine origin.

A commercially available assay ("Dade$^R$ factor VIII Chromogen"; manufacturer: Baxter) is carried out in a manner analogous to the above-mentioned method; also in this case, factor X must be added to the sample in a separate pipetting stage. A disadvantage of this assaying method is to be seen in that it is relatively complex to carry out because of several pipetting stages. This disadvantage, in particular, bears upon screening, since there remains only little time for the operational procedures involved (incubation time: approximately 90 seconds; measuring time: approximately 60 seconds).

The addition of factor X in a separate pipetting stage is necessary because factor IXa activates factor X more rapidly in the presence of calcium ions than without calcium ions. (J. Biol. Chem. 256, 3433–3442 (1981)), what is, of course, undesired. Thus, it is, in principal, not possible with the assaying methods described to initally mix all of the components so as to form a reagent to be added to the sample only afterwards.

According to another test "COATEST®: factor VIIIC"; manufacturer: Kabi Vitrum), a mixture of bovine factors IXa and X with phospholipids, at first, is added to the sample, which mixture must be freshly prepared before assaying. This mixture contains factor X in addition to factor IXa, yet it must not contain any calcium ions in order not to trigger the undesiredly rapid activation of factor X. Therefore, the calcium must be introduced into the sample in a separate pipetting stage after incubation of the sample admixted with the mixture; the reaction is started only by the addition of calcium. After another incubation of 5 to 10 minutes, the chromogenic substrate is added. Thus, a missing component must be added in a separate stage to start the reaction even with this test; complex formation and activation are effected in two stages.

The invention has as its object to provide a reagent by which a simple assaying method of the initially defined kind is feasible in as few pipetting stages as possible. The reagent according to the invention is to be used both for assaying body liquids as to their factor VIII activities and for automatically examining highly purified factor VIII preparations.

The reagent according to the invention for determining factor VIII activity is characterized in that it contains factor IXaβ, factor X, calcium ions, thrombin, phospholipids and, if desired, factor XIa and factor XIIa.

The invention is based on the finding that factor IXaβ (in an aqueous solution) is not capable of activating factor X for a period of some hours even in the presence of calcium ions. Thus, it has become possible to unite all the components necessary for complex formation and activation in a single reagent and to mix the same with the sample in a single pipetting stage. The reagent according to the invention remains stable for hours and, thus, may be prepared without time pressure prior to effecting screening. The presence of additional coagulation factors XIa and XIIa has a stabilizing effect on the complex formed.

Factor IXaβ may be obtained from human plasma in a known manner by treatment with Celite®(manufacturer: Johns-Manville Corp.).

Suitably, a substance (e.g., a tetrapeptide) is added to the reagent in order to avoid clot formation during the assay. Furthermore, it is suitable to add a heparin neutralizing agent (e.g., polybren) to the reagent in order to render the determination of factor VIII independent of the heparin content of the assaying sample.

The invention also relates to a kit comprising two reagent components A and B for preparing the reagent according to the invention, reagent component A containing factors IXaβ and X, thrombin, calcium ions and, if desired, factors XIa and XIIa, and reagent component B containing phospholipids.

The invention, furthermore, relates to a kit comprising two reagent components C and D for preparing the reagent according to the invention, reagent component C containing factors IXaβ and X, calcium ions and, if desired, factors XIa and XIIa, and reagent component D containing thrombin and phospholipids.

A preferred embodiment of the reagent according to the invention consists in that thrombin is present at a concentration ranging between 0.01 and 2.0 U/ml, phospholipids are present within a range of 0.01 to 100 nmol/ml, calcium ions are present within a range of 1 to 50 μmol/ml, factor IXaβ is present within a range of 0.05 and 5 U/ml, factor X is present within a range of 0.01 and 10 U/ml and, if desired, factors XIa and XIIa each are present within a range of 0.01 to 2.0 U/ml.

Suitably, the factors and the thrombin contained in the reagent according to the invention are of human origin and not of bovine origin, if human factor VIII activity is to be determined by aid of the reagent of the invenion. It is a principle of biochemical analytics to assay equivalent things wherever possible in order to exclude error sources, which have proved to occur when using generically different reaction partners. This disadvantage is particularly imminent if the samples to be assayed have high factor VIII activities, which is of interest in the industrial quality control of highly purified factor VIII preparations.

The use of bovine coagulation factors also bears the risk that the proteins contained will be contaminated, a precise and complex documentation of the origin of such factors, thus, being required (certificate of the freedom of epidemics of the cattle, including the non-infectedness of the bovine plasma obtained from bovine blood).

If desired, the proteins contained in the reagent according to the invention have been subjected to a treatment for inactivation of possibly present infectious agents. Such inactivation methods, for instance, are known from EP-A 0 159 311 as well as from EP-A 0 050 061 and from EP-A 0 131 740. They guarantee that the concentrates will be largely free of infectious agents.

3

The invention also relates to a method of determining factor VIII activity in a sample by reaction with the reagent according to the invention, wherein activated factor X (factor Xa) is at first formed as a function of the factor VIII content and factor Xa is determined quantitatively afterwards. This determination may, for instance, be carried out in a manner that factor Xa at first is reacted with a chromogenic substrate to release a substance, which is determined spectrophotometrically.

The method of the invention has an incubation time of about five minutes, thus rendering easily feasible both manual operations and operations at automatic analyzers typically used in screening.

Furthermore, it has proved that the photometric measurement may take place for a period of time of even up to four minutes, because the color development occurs linearly within this period of time (release of p-nitroaniline from the chromogenic substrate); the reagent according to the invention, thus, has the favorable property of releasing at a constant speed and during a period of more than four minutes the substance to be determined spectrophotometrically. This period of time is unusually long as compared to presently known reagents (with the assay "Dade$^R$ Faktor VIII Chromogen" (manufacturer: Baxter) it is only about one minute).

The invention will be explained in more detail by the following examples.

Preparation of Reagent (1) Factor IXaβ solution: 1 l citrated plasma is mixed with 25 ml 1 molar $CaCl_2$ solution for the preparation of human serum and is allowed to stand at room temperature over night; the clot formed is squeezed out and discarded. The serum is filtered and frozen.

For the adsorption of factor IXaβ from human serum, the latter is thawed at 37° C. 0.5 mg/ml Sephadex$^R$ A 50 (manufacturer: Pharmacia) is added, stirred and filtered. Subsequently, the gel is eluted in a buffer (2.5% of the serum volume; 30 g/l NaCl, 4 g/l $Na_3$ citrate.$2H_2O$, pH 7.0). The eluate serves as the factor IXaβ solution.

(2) Factor X solution: A concentrated solution of prothrombin complex factors II, IX, X is packed on dextrane sulfate sepharose and eluted with an ionic strength gradient (0.1–1 I). The fractions are assayed for their factor X contents. Those fractions which contain factor X are pooled, concentrated by ultrafiltration and frozen. Concentration: about 30 U factor X/ml.

(3) Celite eluate: Citrated plasma is mixed with 2% by weight of Celite and incubated at 37° C. under shaking. Subsequently, it is centrifuged at 3000 rpm for 5 to 10 minutes (room temperature). The supernatant is discarded. The Celite sediment is washed three times with physiologic NaCl solution and then is eluted with 10 % NaCl solution (¼ volume of the starting plasma) and centrifuged. The supernatant is filled into dialysis tubes and dialyzed against the at least 20-time volume of physiologic NaCl solution at 4° C. over night and subsequently is frozen.

To prepare reagent component A, the following components are mixed:

| | |
|---|---|
| Imidazol buffer | 15.6 ml |
| (1.5 g/l imidazol; 9 g/l NaCl; 0.1% albumin, pH 8.3) | |
| Celite eluate | 1.05 ml |
| Factor IXaβ solution | 1.2 ml |
| Factor X solution | 0.3 ml |
| 20% human albumin | 0.9 ml |
| $CaCl_2$ 25 mmol/l | 18.0 ml |
| Thrombin | 0.12 ml |

This mixture is dialyzed against a buffer (1.36 g/l imidazol, 2.34 g/l NaCl, 1.47 g/l sodium citrate, 13 ml 1 mol/l $CaCl_2$) at 4° C. over night and subsequently is filtered. A coagulation-active phospholipid concentrate is diluted 1:200 with dialysis buffer and 1 part of this solution (reagent component B) is mixed with 3 parts of the filered mixture. After the addition of 0.19% Tween 20 (polyoxyethylene sorbitane monolaureate) and 5 mg tetrapeptide AcOH-Gly-Pro-Arg-Pro-OH, the reagent is filled into containers of 2 ml each.

Determination of Factor VIII in Sample:

At first, 1 part of a factor Xa substrate solution ($CH_3OCO$-D-CHA-Gly-Arg-pNA.AcOH, 4 mmol/l) is mixed with 2 parts of a reaction buffer (6.06 g/l Tris; 3.03 g/l EDTA; 25 g/l NaCl; 4 ATU/ml hirudin; pH 8.2) (substrate buffer mixture).

Pipetting scheme:

50 µl of a factor VIII containing sample and 250 µl reagent are incubated at 37° C. for 5 min and mixed with 300 µl substrate buffer mixture.

The spectrophotometric determination of factor VIII is effected in a manner known per se, the measurement of the solution being carried out after three minutes at 405 nm (37° C.). The establishment of the reference curve likewise is effected in a known manner by starting from a lyophilized normal plasma pool that is to contain 1 IU factor VIII/ml after reconstitution with aqua dest.

It has proved that the assaying method according to the invention exhibits a linear interrelationship between the increase in extinction per time unit and the factor VIII content within a concentration range of between 2 IU/ml and 0.002 IU/ml.

The assaying method according to the invention exhibits a high sensitivity and, for this reason, is suited also for the indirect assessment of proteins reacting with factor VIII (activated or not activated). Thus, it is, for instance, possible, to indirectly assess the content of activated protein C and its co-factor (protein S) or factor VIII inhibitor by adding a predetermined excess amount of factor VIII (activated or not activated), whereupon the portion of factor VIII not inhibited by the activated protein C and its co-factor or factor VIII inhibitor is assessed.

The method according to the invention, thus, also may be applied to indirectly assaying factor VIII inhibiting activity.

Determination of Activated Protein C (aPC)

Reagent components A and B are used in the manner already described in the production of the reagent.

75 µl factor VIII solution (5 U/ml) are activated by adding 35 µl thrombin solution (0.5 U/ml) and 5 minutes of incubation at 37° C. 50 µl of the sample solution having different aPC contents (0.03; 0.10; 0.30; 1.00 U/ml) are mixed with 100 µl incubation mixture in the presence of 200 µl buffer mixture (5 ml Tris buffer, pH 7.4; 100 µl hirudin and 25 µl phospholipid reagent component B) and incubated at 37° C. for 2 minutes. After the addition of 200 µl reagent component A to 100 µl of the incubated sample solution and subsequent incubation (5 min at 37° C.) the portion of factor VIII not inhibited by aPC is photometrically determined. The sample is admixed with the substrate buffer mixture already described. The extinction at 405 nm is measured at 37° C. for 3 minutes. There is a linear interrelationship between the increase in extinction with time (E/min) and the concentration of aPC in the sample solution.

| Concentration of aPC (U/ml) | E/min |
|---|---|
| 0 | 0.245 |
| 0.03 | 0.243 |
| 0.10 | 0.239 |
| 1.00 | 0.119. |

What we claim is:

1. A composition for determining factor VIII activity in a sample, which composition comprises, in a single reagent, from 0.05 to 5 U/ml of factor IXaβ, from 0.01 to 10 U/ml of factor X, from 1 to 50 μmol/ml of calcium ions, from 0.01 to 2.0 U/ml of thrombin, and from 0.01 to 100 nmol/ml of phospholipids.

2. A composition as set forth in claim 1, further comprising factor XIa and factor XIIa.

3. A composition as set forth in claim 2, wherein each of factors XIa and XIIa is present within a range of 0.01 to 2.0 U/ml.

4. A composition as set forth in claim 1, 2, or 3, wherein said factors IXaβ and X and said thrombin contained in said composition are of human origin.

5. A composition as set forth in claim 4, wherein said factors IXaβ and X and said thrombin have been subjected to a treatment for inactivation of any infectious agents present.

6. A reagent component for producing the composition of claim 1, which reagent component comprises factor IXaβ, factor X, thrombin and calcium ions, in amounts to render the composition effective to measure factor VIII activity.

7. A reagent component as set forth in claim 6, wherein said factors IXaβ and X and said thrombin are of human origin.

8. A reagent component as set forth in claim 7, wherein said factors IXaβ and X and said thrombin have been subjected to a treatment for inactivation of any infectious agents present.

9. A kit comprising a first reagent component A and a second reagent component B, which kit upon admixture of reagent components A and B, produces the single reagent composition of claim 1, said reagent component A containing factors IXaβ and X, thrombin and calcium ions, and said reagent component B containing phospholipids, the amounts of the constituents of said reagent components A and B rendering the single reagent composition produced therefrom effective to measure factor VIII activity.

10. A kit as set forth in claim 9, wherein said reagent component A further contains factors XIa and XIIa.

11. A kit comprising a reagent component C and a reagent component D, which kit, upon admixture of reagent components C and D, produces the single reagent composition of claim 1, said reagent component C containing factors IXaβ and X and calcium ions, and said reagent component D containing thrombin and phospholipids, the amounts of the constituents of said reagent components C and D rendering the single reagent composition produced therefrom effective to measure factor VIII activity.

12. A kit as set forth in claim 11, wherein said reagent component C further contains factors XIa and XIIa.

13. A kit as set forth in claim 9, 10, 11 or 12, wherein said factors and said thrombin contained in said kit are of human origin.

14. A kit as set forth in claim 13, wherein said factors and said thrombin have been subjected to a treatment for inactivation of any infectious agents present.

15. A method of determining factor VIII activity in a sample comprising:

(a) reacting said sample with a single reagent comprising factor IXaβ, factor X, thrombin, calcium ions and phospholipids, whereby complex formation and activation of factor X occur in a single incubation step, the amount of activated factor X formed being a function of the activity of factor VIII present in the sample;

(b) measuring the amount of activated factor X produced by the reaction; and (c) determining the factor VIII activity based on the amount of activated factor X.

16. A method of determining factor VIII activity according to claim 15, wherein the amount of activated factor X produced is measured by adding a chromogenic substrate which reacts with activated factor X and measuring the absorbance produced by the reacted chromogenic substrate, which absorbance is a function of the amount of activated factor X.

17. A method of determining proteins reacting with factor VIII, said proteins comprising protein C and ire co-factor protein S, factor VIII antibodies and factor VIII inhibiting proteins, by using a single reagent composition which comprises factor IXaβ, factor X, calcium ions, thrombin and phospholipids, in amounts effective to measure factor VIII activity, wherein an excess amount of factor VIII is added to said sample and reacted therewith by inhibiting part of said factor VIII and leaving a remaining amount of factor VIII, said factor X is activated by said remaining amount of factor VIII, and said factor VIII is determined by measuring the amount of activated factor X.

18. A method as set forth in claim 17, further comprising adding an amount of factor VIII to said reagent.

* * * * *

UNITED STATES PATENT AND TRADEMARK OFFICE
CERTIFICATE OF CORRECTION

PATENT NO. : 5,506,112

DATED : April 9, 1996

INVENTOR(S) : Lang et al.

It is certified that error appears in the above-indentified patent and that said Letters Patent is hereby corrected as shown below:

Title page, first col., 5th-from-bottom line, "2/1985" should read -- 10/1985 --. Col. 1, line 50, "admixted" should read -- admixed--. Col. 6, line 40, "ire" should read -- its --.

Signed and Sealed this

Tenth Day of September, 1996

Attest:

Attesting Officer

BRUCE LEHMAN

Commissioner of Patents and Trademarks